(12) United States Patent
Ramamoorthy (10) Patent No.: US 11,286,464 B2
(45) Date of Patent: Mar. 29, 2022

(54) VIRAL VACCINES AND METHODS OF FORMING THE SAME

(71) Applicant: NDSU Research Foundation, Fargo, ND (US)

(72) Inventor: Sheela Ramamoorthy, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 0 days.

(21) Appl. No.: 15/906,685

(22) Filed: Feb. 27, 2018

(65) Prior Publication Data

US 2018/0245053 A1 Aug. 30, 2018

Related U.S. Application Data

(60) Provisional application No. 62/463,971, filed on Feb. 27, 2017.

(51) Int. Cl.
| | |
|---|---|
| *C12N 7/00* | (2006.01) |
| *A61K 39/145* | (2006.01) |
| *A61K 39/215* | (2006.01) |
| *A61P 31/16* | (2006.01) |
| *A61K 39/12* | (2006.01) |
| *A61P 31/14* | (2006.01) |
| *A61K 39/00* | (2006.01) |

(52) U.S. Cl.
CPC ............... *C12N 7/00* (2013.01); *A61K 39/12* (2013.01); *A61K 39/145* (2013.01); *A61K 39/215* (2013.01); *A61P 31/14* (2018.01); *A61P 31/16* (2018.01); *A61K 2039/5252* (2013.01); *A61K 2039/543* (2013.01); *C12N 2760/16134* (2013.01); *C12N 2760/16163* (2013.01); *C12N 2770/20034* (2013.01); *C12N 2770/20063* (2013.01); *C12N 2770/24134* (2013.01)

(58) Field of Classification Search
None
See application file for complete search history.

(56) References Cited

U.S. PATENT DOCUMENTS

| | | | | |
|---|---|---|---|---|
| 3,060,094 A | * | 10/1962 | Dutcher | ............... A61K 39/17 424/204.1 |
| 10,034,934 B2 | * | 7/2018 | Marthaler | ............ A61K 39/215 |

OTHER PUBLICATIONS

Jung et al. (The Veterinary Journal, 2015, p. 134-143).*
Victoria et al. (Journal of Virology, 2010, vol. 84, p. 6033-6040).*
Jang et al. (Veterinary Microbiology, 2019, vol. 231, p. 120-128).*
Fedorowa et al. (Vaccine 2012, p. 2973-2980).*
Baek et al. (Veterinary Immunology, 2016, p. 45-49).*
Marazzi et al (Nature et al., vol. 483, p. 428-433).*

* cited by examiner

*Primary Examiner* — Agnieszka Boesen
(74) *Attorney, Agent, or Firm* — Stites & Harbison, PLLC; Mandy Wilson Decker; Sean P. Ritchie (57) ABSTRACT

Provided herein is a method for producing an inactivated virus including a) heating the virus to a temperature sufficient to disrupt the virus membrane; b) exposing the virus of step (a) to an RNA degrading enzyme; and c) cooling the virus to a temperature sufficient to reestablish the integrity of the virus membrane. Also provided herein is a vaccine produced using the instant method.

18 Claims, 7 Drawing Sheets

VIRAL VACCINES AND METHODS OF FORMING THE SAME

RELATED APPLICATIONS

This application claims priority from U.S. Provisional Application Ser. No. 62/463,971, filed Feb. 27, 2017, the entire disclosure of which is incorporated herein by this reference.

GOVERNMENT INTEREST

This invention was made with government support under grant numbers 2014-31100-06038 and 2016-31200-06038 awarded by the United States Department of Agriculture/National Institute of Food and Agriculture (USDA/NIFA). The government has certain rights in the invention.

TECHNICAL FIELD

The presently-disclosed subject matter generally relates to vaccines and methods of forming the same. More specifically, the presently-disclosed subject matter relates to viral vaccines and methods of forming the same.

BACKGROUND

Although viruses are extremely simple microorganisms composed of a protein shell (capsid) and genetic material which can be either DNA or RNA (depending on the type of virus), they cause some of the deadliest human and animal diseases. Based on the inherent chemical nature of DNA and RNA molecules and the fidelity of the enzymes required to generate them, RNA is less stable and more error prone than DNA. Therefore, RNA viruses tend to accumulate high rates of mutation, are generally more genetically diverse than DNA viruses, and are more prone to rapid changes that may lead to reduced vaccine efficacy. One example includes the common situation where a 'flu shot' is against the 'wrong' virus. This is caused by the virus mutating after the vaccine development started, and changing enough in just a few months that the vaccine loses effectiveness in preventing infection. Often, the new strains are antigenically distinct from the previously circulating strains, due to mutations in the structural components. Therefore, prior vaccination or exposure to the agent does not prevent infection by the new strain.

Over the last few decades, changing practices in global trade, travel, animal/human movement and proximity have facilitated to the emergence and spread of new infectious diseases or the reemergence of previously controlled diseases, at the rate of about 3 per year. The more commonly known diseases which caused widespread infections, and even more widespread fear include, HIV/AIDS, SARS, the 2009 swine influenza (SIV), avian influenza (AIV), chikungunya, West Nile, Ebola hemorrhagic fever, and more recently, the Zika virus. Of note, a majority of these emerging or re-emerging diseases are caused by RNA viruses. The socio-economic impact of outbreaks range from loss or diminished quality of life, to worldwide pandemics which place a huge burden on healthcare systems and disrupt trade and travel to cause severe economic losses. For example, the SARS pandemic is estimated to have caused a loss of $30 billion in 2003, although only about 8000 cases were identified.

Similarly, in veterinary medicine, intensive farming practices, including livestock movement and intermingling, have preceded the increasing emergence and evolution of infectious diseases. In the context of the instant inventors experience and expertise in veterinary vaccinology, especially swine medicine, the porcine respiratory and reproductive disease syndrome virus (PRRSV), swine influenza (SIV) viruses, Seneca valley virus, porcine epidemic diarrhea virus (PEDV), porcine delta coronavirus (PDCV), porcine circoviral associated diseases (PCVAD), and rota viral diarrheas are viral diseases which emerged in the last few decades. As with the human diseases, a majority of the emerging animal pathogens are RNA viruses. For example, the porcine epidemic diarrhea virus (PEDV) is a RNA virus and an enteric swine coronavirus. It emerged in the U.S in 2013 and spread rapidly to all the major swine production states. In 2014, PEDV was responsible for the death of a quarter of the U.S. swine population, leading to an industry loss of $540 million in 10 months. In the following year, two other new swine coronaviruses emerged. Not only do these emerging animal pathogens have the potential to spread quickly and/or cause significant financial loss, many animal diseases can cross species boundaries to cause deadly human infections e.g. influenza, yellow fever, west Nile, and rabies. Both West Nile and Hanta Virus are endemic to North Dakota.

Vaccines are the mainstay of public health measures for the prevention of infectious diseases. Of over 200 human infections, the World Health Organization (WHO) lists only 25 as vaccine-preventable. Vaccine development is either inadequate or completely absent for the others, largely due to a lack of the exact understanding of what it takes to develop an effective vaccine. For example, the identification of the exact viral antigens which elicit protection without compromising immunity, the precise immune mechanisms which are required to clear infection, and the means to target them are all challenging areas of vaccinology. As a consequence, a majority of the currently available commercial human and veterinary vaccines are developed with "first-generation" technology, where the entire killed or attenuated microorganism is administered as a vaccine.

There are primarily two types of first-generation vaccines; inactivated or killed vaccines and attenuated or live vaccines. Inactivation is generally achieved by subjecting the viral particles to chemical treatment, while attenuation can be achieved by adapting the virus to an irrelevant host or using genetic engineering to mutate specific regions of the genome which are responsible for virulence. Although a major advantage of inactivated vaccines is that they are extremely safe, they are often ineffective against RNA viruses and may not induce complete or long-lasting protection. Additionally, with inactivated vaccines, multiple vaccinations are generally required to maintain protection. Given the genetic/antigenic complexity of RNA viruses, coupled with immuno-subversive mechanisms employed by them for their survival, a majority of the more effective vaccines against RNA viruses are of the attenuated type. However, while live and/or attenuated vaccines can induce long-term protection with a single dose and are generally more efficacious, they can potentially revert to virulence or recombine with field strains to produce new strains of the agent. As such, live or attenuated vaccines have a lower margin of safety. An effective vaccine would therefore, ideally combine the safety and efficacy advantages of inactivated and attenuated vaccines.

In veterinary medicine, autogenous or custom-made vaccines are frequently used against infectious agents for which vaccine development is ineffective. Autogenous vaccines are prepared by collecting infectious material from a specific herd by the producer or veterinarian, culturing the material in the lab and administering it exclusively to the originating herd, either after inactivation or as a live preparation. While neither the efficacy nor the safety of autogenous vaccines is guaranteed, their popularity is based entirely on an enormous industry need to prevent the infectious disease. As mentioned before, agents which are highly mutable and emerge periodically as new strains, and which are not covered by the protective umbrella of licensed vaccines, are frequently candidates for autogenous vaccine development. Licensing requirements for autogenous vaccines are less stringent. Temporary authorization of experimental or conditionally licensed vaccination in emergency situations is also not unusual in veterinary medicine. For example, in swine medicine, PRRSV, swine influenza, rota viruses, and bacterial pathogens like *Mycoplasma* sp., *Actinobacillus* sp., *Streptococcus*, and *Clostridia* are candidates for autogenous vaccines. In cattle, agents which cause respiratory illness and pink eye (endemic to North Dakota) are often candidates for autogenous vaccines.

Similarly, a process called planned exposure, which is associated with similar safety and efficacy risks, is employed for swine viruses such as PRRSV and PEDV. Essentially, serum or fecal matter from infected animals is administered as a crude immunogen or vaccine in naïve animals, mostly by the producers themselves. A loss of 10-20% of the herd is accepted as a better risk than the alternative of losing a higher percentage to a full-blown outbreak. The planned exposure process is, therefore, less controlled than the use of autogenous vaccines.

Regardless of the type of vaccine, the lead development time for fully licensed vaccines can typically take several years, after the emergence of the pathogen. The longer the delay in the availability of detection and control measures, the greater the dissemination and damage due to the new agent. The extent of damage can be exacerbated by ongoing genetic evolution, especially for RNA viruses, which may result in vaccines being ineffective or partially effective when they finally become available. Accordingly, there remains a need for the development of safe and effective rapid-response vaccines in both human and animal medicine. The availability of such rapid-response vaccine technology also has important implications for combating bioterrorism and advancing national defense.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments, the presently-disclosed subject matter is directed to a method for producing an inactivated virus including a) heating the virus to disrupt the virus membrane; b) exposing the virus of step (a) to a ribonucleic acid (RNA) degrading enzyme; and c) cooling the virus to reestablish the integrity of the virus membrane. In one embodiment, the virus is porcine epidemic diarrhea virus.

In some embodiments, disrupting the virus membrane comprises forming pores in the virus membrane. In some embodiments, disrupting the virus membrane comprises temporarily denaturing the virus membrane. In one embodiment, the heating of step (a) is to a temperature of at least 42° C. In another embodiment, the heating of step (a) is for at least 10 minutes.

In some embodiments, the RNA degrading enzyme is RNase. In some embodiments, the exposing of step (b) includes exposing the virus to a solution that contains the RNA degrading enzyme. In one embodiment, the solution includes at least two RNA degrading enzymes. In another embodiment, the at least two RNA degrading enzymes comprise RNase A and RNase H. In some embodiments, the exposing of step (b) includes forming an equilibrium of the concentration of the RNA enzyme inside and outside the virus. In some embodiments, the exposing of step (b) is for at least 4 hours. In another embodiment, the modifying includes acetylation. In some embodiments, the exposing of step (b) destroys viral genetic material without damaging immunogenic capsid antigens of the virus.

In some embodiments, the cooling of step (c) is to a temperature of 4° C. or less. In some embodiments, the cooling of step (c) is for at least 3 hours.

In some embodiments, after step (a) and before step (b), the method further includes modifying a protein within the virus. In one embodiment, the modifying relaxes an RNA:protein association to expose the RNA.

Also provided herein, in some embodiments, is a method for producing an inactivated virus including a) heating the virus to a temperature of at least 42° C. for at least 10 minutes to disrupt the virus membrane; b) exposing the virus of step (a) to a ribonucleic acid (RNA) degrading enzyme; and c) cooling the virus to a temperature of 4° C. or less for at least 3 hours to reestablish the integrity of the virus membrane.

Further provided herein, in some embodiments, is a virus vaccine produced by a) heating the virus to disrupt the virus membrane; b) exposing the virus of step (a) to a ribonucleic acid (RNA) degrading enzyme; and c) cooling the virus to reestablish the integrity of the virus membrane.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter includes viral vaccines and methods of producing viral vaccines. Provided herein, in some embodiments, is a method for producing an inactivated virus. In one embodiment, the method includes a) heating the virus to a temperature sufficient to disrupt the virus membrane; b) exposing the virus of step (a) to an RNA denaturing and/or degrading enzyme; and c) cooling the virus to a temperature sufficient to reestablish the integrity of the virus membrane. Also provided herein, in some embodiments, is a vaccine produced according to one or more of the instant embodiments.

As noted above, in one embodiment, the method includes disrupting the virus membrane through heating of the virus. In another embodiment, disrupting the virus membrane includes forming pores or temporarily denaturing the membrane. The temperatures and timing for disrupting the virus membrane will depend upon the specific virus. For example, for porcine epidemic diarrhea virus (PEDV), suitable temperatures include, but are not limited to, up to about 42° C., about 42° C., at least about 40° C., at least about 42° C., at least about 44° C., between about 40° C. and about 44° C., or any combination, sub-combination, range, or sub-range thereof Suitable timing for PEDV includes, but is not limited to, at least 1 minute, at least 5 minutes, at least 10 minutes, at least 30 minutes, up to 1 hour, up to 4 hours, up to 8 hours, up to 12 hours, between 1 minute and 12 hours, or any combination, sub-combination, range, or sub-range thereof. Suitable temperatures for other viruses may be lower than, the same as, or higher than the aforementioned temperatures for PEDV. Similarly, suitable timing for other viruses may be less than, the same as, or higher than the aforementioned timing for PEDV.

The disruption of the virus membrane according to step (a) permits small molecules, such as enzymes, to enter the virus. In some embodiments, this disruption permits the RNA denaturing and/or degrading enzyme of step (b) to pass through the virus membrane. In one embodiment, step (b) includes exposing the virus to a solution that contains the RNA denaturing and/or degrading enzyme in a sufficient concentration to allow the RNA enzyme to pass through the denatured virus membrane resulting from step (a). In another embodiment, the virus is exposed to the solution of RNA enzyme in step (b) for a sufficient time to allow an equilibrium of the concentration of RNA enzyme inside and outside the virus. Suitable RNA denaturing and/or degrading enzymes include, but are not limited to, RNase or any other enzyme that has the ability to denature or degrade RNA. As will be appreciated by those skilled in the art, steps (a) and (b) may be performed in any order so long as the denatured virus membrane is exposed to the RNA enzyme at some point. For example, the virus may be heated to denature the virus membrane first and then exposed to the RNA enzyme while the virus membrane is still denatured, or the virus may be exposed to the RNA enzyme and then heated to denature the virus membrane while remaining exposed to the RNA enzyme.

Additionally or alternatively, in certain embodiments, the virus includes one or more proteins closely associated with the RNA thereof. For example, the influenza NS1 protein is closely associated with the viral genome in influenza, mimicking the histone:DNA association in human genomes. Accordingly, in some embodiments, the method includes disrupting an RNA:protein interaction in the virus prior to exposing the virus to the RNA enzyme. In one embodiment, disrupting the RNA:protein interaction includes chemically modifying the protein associated with the RNA. In another embodiment, the chemical modification of the protein includes methylation and/or acetylation. In a further embodiment, the protein includes histone, a histone-like protein (e.g., influenza NS1 protein), or any other protein that closely associates with the RNA of the virus. The chemical modification of the protein, such as, for example, the chemical modification of NS1 with a histone acetylase enzyme, relaxes the RNA:protein association and exposes the genetic material. By exposing the genetic material, the disruption of the RNA:protein interaction permits the RNA denaturing and/or degrading enzyme to digest the viral RNA.

Following the heating and exposing steps, step (c) of the method disclosed herein includes cooling the virus to a temperature and for a time sufficient to cause the virus membrane to reform. For example, in some embodiments, cooling the virus to a temperature of about 4° C. causes the virus membrane to renature and reform into the form it was before the first step of the method. Although the example above discusses a temperature of about 4° C., as will be appreciated by those skilled in the art, the disclosure is not so limited and may include any other suitable temperature for reforming the virus membrane. Such suitable temperatures will depend upon the specific virus, and may be lower than, the same as, or higher than 4° C.

Without wishing to be bound by theory, it is believed that partially or completely destroying the viral genetic material by degrading the virus membrane and exposing the virus to RNA degrading enzymes, without damaging the immunogenic capsid antigens, produces a vaccine candidate which will enter host cells and can undergo abortive to no replication while still inducing effective immunity due to antigen presentation that resembles natural infection or vaccination with an attenuated vaccine. This process is interchangeably referred to herein as inactuation. In addition, it is believed that the vaccines produced according to one or more of the embodiments disclosed herein provide vaccination without causing any disease or other adverse effect. Accordingly, in some embodiments, the vaccines disclosed herein combine the safety and efficacy advantages of inactivated and attenuated vaccines respectively, to generate rapid, first-response vaccines.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

Influenza A virus (Sandbulte, Spickler, Zaabel, & Roth) can be regarded as a prototype virus for the "one-health" concept as it can cross species boundaries with ease; affecting swine, humans, birds, horses as well as pet animals. Despite the concerted effort and investment in influenza vaccine research, the efficacy of influenza vaccines is limited by the accurate prediction of circulating strains for each season. Immunity is short-lived and annual vaccinations are recommended. With changing travel and trade practices, influenza pandemics occur roughly once in every ten years now, compared to once in 30-50 years in the 1800's. The 2009 pandemic caused by the Influenza/A/H1N1 virus (pH1N1) was believed to be of swine origin. The virus was hence dubbed the "swine flu" (swine influenza virus—SIV). It caused widespread panic and affected the export and trade of pork products, while health care systems, worldwide, were overwhelmed.

Avian influenza (AIV) is ranked among the highest emerging infectious disease risks for both animals and humans due to the very high rates (over 50%) of mortality in humans with the highly pathogenic strains (HPAI). While human to human transmission of the avian influenza strains is not the norm historically, the emergence of a strain which is transmitted between humans is possible. Should this occur, it would likely lead to a public health nightmare. The 2014-15 AIV outbreak affected 21 states in the U.S, including Minnesota, and cost the industry $3.3 billion (McKenna, 2015). Hence, the availability of technology to develop rapid-response vaccines against influenza viruses is a significant need for both human and veterinary medicine.

This example describes a method of producing a vaccine according to the instant disclosure. More specifically, this example describes an experiment testing the efficacy of the inactivated pH1N1 vaccine in a swine challenge model.

All animal experimentation was carried out at the biosafety level 3 (BSL3) swine experimentation facilities at SDSU. Two groups of twelve, 3-4-week-old pigs were randomly assigned to the treatment and negative control groups and housed separately. Pigs were vaccinated with $10^4$ $TCID_{50}$ of the inactivated IAV (2 ml intra-nasally and 2 ml intra-muscularly) and boosted by the same route two weeks later. Serum (to assess antibody responses) and nasal swabs (to assess viral shedding) were collected every week. To assess cell-mediated immunity, whole blood samples were collected prior to immunization and challenge with the virulent virus. Antibody responses were assessed by a standard hemagglutination inhibition (USDA) test, every week post vaccination. A third booster was administered if the HI titers were less than 1:32 at week 4. To assess vaccine safety, 4 animals from each group were euthanized prior to challenge with the live virus. It was expected that vaccination would not produce any adverse effects at the vaccination site or cause clinical signs or lung lesions characteristic of IAV.

Two approaches were used to achieve inactivation of PEDV. In the first approach, virus cultures were exposed to gamma irradiation based on the hypothesis that the viral genetic material would be destroyed while the antigenic structures would remain intact. However, it was found that the irradiation approach may destroy viral antigenic structure and interfere with immune responses. The second approach was to expose the virus to heat to relax the capsid (shell), followed by RNase treatment genome and then treatment at 4° C. to refold the capsid. RNase is an enzyme which can selectively destroy the RNA genome of the virus.

Validation of the inactivation process by electron microscopy showed intact viral structures following both treatments. An assessment of the integrity of the viral RNA genome by PCR showed that both processes resulted in the fragmentation of the genome, while detection of viral RNA within cells showed that the inactivated virus was entering host cells in a manner similar to the live virus. Vaccination of the pigs with the vaccine candidates induced strong virus neutralizing antibody responses in the group immunized with the heat+RNase treated virus, while the responses were not as strong with the irradiated vaccine. Examination of virus shedding and intestinal pathology following challenge with the virulent virus showed similar patterns, with the heat+RNase treated vaccine inducing excellent protection and no detection of virus shedding or intestinal lesions while the irradiated vaccine was less protective. The safety margin of both process with very high, with no detection of vaccine virus shedding in fecal matter at any time of the experiment and no lesions being produced in vital organs or injection sites. In conclusion, the approach of using heat+RNase treatment for the development of first response vaccines against PEDV shows strong potential for commercialization and application to other viral pathogens.

Results

Inactuation of PEDV Cultures.

Two approaches were followed to achieve optimal inactuation. Viral cultures of PEDV were re-suspended in DMEM to $10^5$ $TCID_{50}$ viral particles/ml and subjected to either a) gamma-irradiation for 24 hours or an equivalent of 10.85 KGy, or b) 42° C. for 10 mins, followed by 2 mg/ml of RNase A and 10,000 units/ml of RNase H and incubated at 42° C. for 4 hours. The inactuated culture was then placed at 4° C. for a minimum of 3 hours for refolding. Untreated virus cultures were used as controls in both cases.

The Inactuation Process Maintains Viral Structural Integrity.

Assessment of the inactivated viral cultures by transmission electron microscopy (TEM) showed that the viral capsid structures remained intact in both the irradiation and heat/RNase treatments (FIGS. 1A-3C). An untreated viral culture was used as a control. As expected, the processes used did not damage the antigenic structures which are important for vaccine-induced immunity.

Inactuation Diminishes Viral Replication.

Figure 1A:
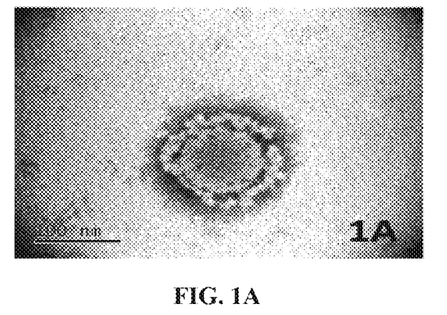
FIGS. 1A-B show TEM images of a single untreated control PED virion (A) and a cluster of untreated control PED virions (B), illustrating the characteristic icosahedral shape and surface spikes.
Figure 1B:
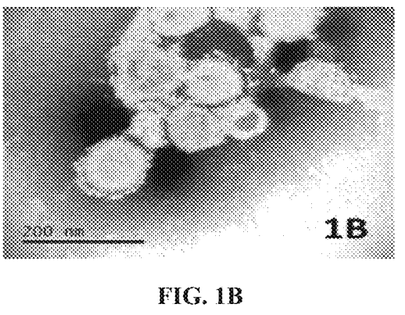
Figure 2A:
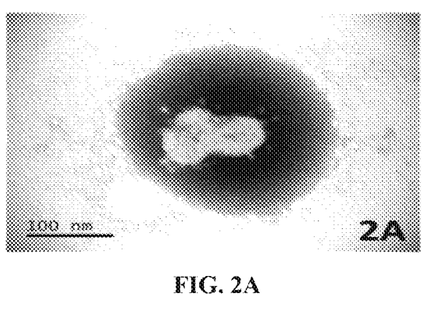
FIGS. 2A-B show TEM images of a single gamma irradiated PED virion (A) and a cluster of gamma irradiated PED virions (B).
Figure 2B:
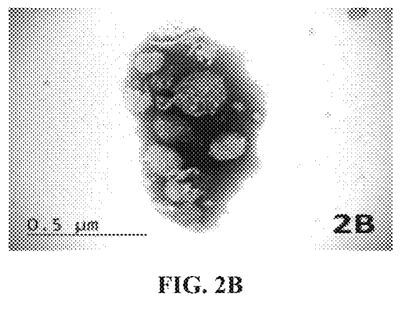
Figure 3A:
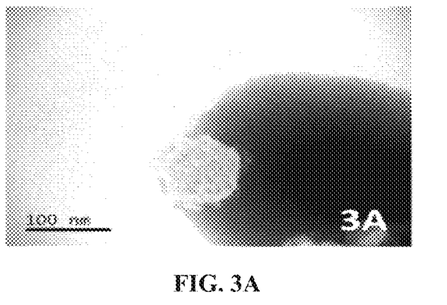
FIGS. 3A-B show TEM images of a single heat/RNase treated PED virion (A) and a cluster of heat/RNase treated PED virions (B).
Figure 3B:
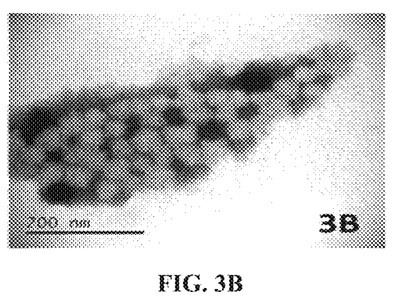
Figure 4A:
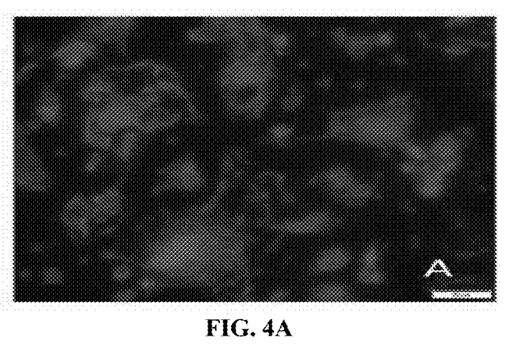
FIGS. 4A-C show immunofluorescence images of inactuated PEDV cultures. Treated and untreated virus cultures were used to infect vero cell monolayers for 3 passages. Viral replication was assessed by staining the cell sheet with a PEDV-specific swine polyclonal antibody, followed by anti-swine FITC conjugate. (A) Untreated PEDV infected cells at passage 3, showing typical cytoplasmic, apple green fluorescence and the formation of syncytia. (B) Irradiated PEDV culture at passage 3, showing no viral growth. (C) Heat and RNase treated PEDV culture at passage 3, showing minimal replication.
Figure 4B:
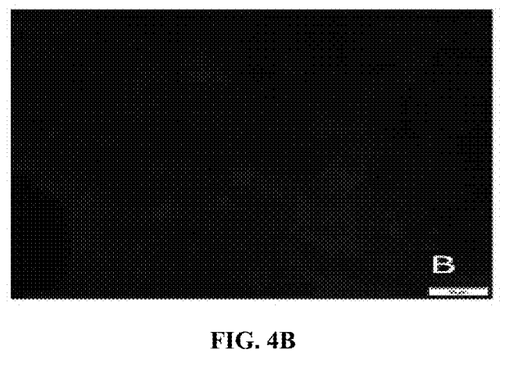
Figure 4C:
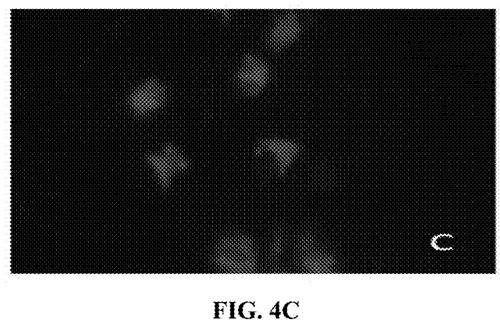

To test the hypothesis that the inactivation process would abrogate or diminish viral replication significantly, Vero cell monolayers were infected with the inactivated viruses and passaged serially three times. This "amplification" test is commonly used to determine whether the virus can replicate after the treatment, as the number of viral particles will increase in each passage to detectable levels. All three passages and an untreated control virus inoculum were examined by immunofluorescent microscopy to determine the extent of viral replication. No viral replication was detected in any of the three passages of the irradiated virus culture, while very slight replication (in comparison to the untreated control) was detected only in the third passage of the heat+RNase treatment (FIGS. 4A-C). Since the post-treatment viral replication was not robust, the likelihood of the vaccine virus being safe in the host was expected to be high.

Antigen Presentation of Inactivated Viral Particles is Similar to that of Natural Infection.

Figure 5:
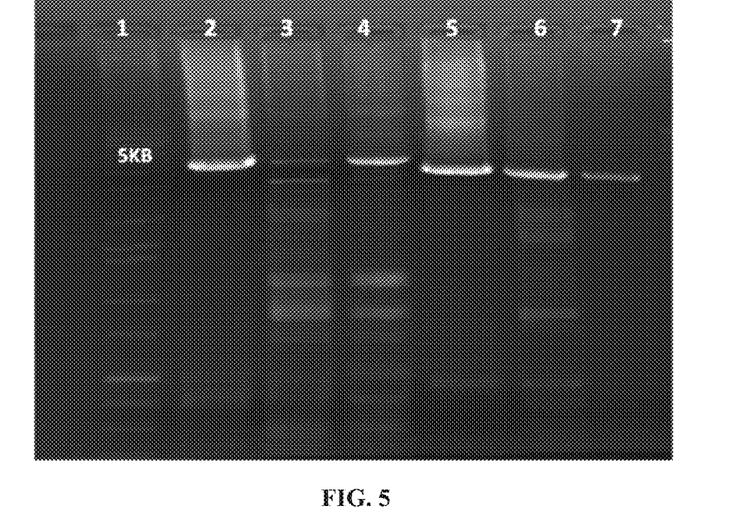
FIG. 5 shows PCR detection of inactuated viral particles in infected cells. By column, the PCR shows (1) Ladder; (2) PEDV untreated control—5 Kb primers; (3) PEDV Heat/

To ensure that the inactivation treatments did not affect the ability of the viral particle to enter cells, but damaged the integrity of the nucleic acids, the inactivated viral cultures were used to infect Vero cells. After thorough washing to remove the inocula, the cell monolayers were subject to PCR analysis to detect the presence of the virus (FIG. 5). As expected, viral cDNA bands of approximately 5 Kb and 3.5 Kb were detected by PCR, indicating the inactivated viral particles had entered the cells. Several bands of smaller sizes were also detected in the cells infected with the inactivated viruses, indicating that the treatments caused fragmentation of the parent RNA strands, as expected.

Assessment of Immune Responses and Vaccine Efficacy in Pigs.

Figure 6:
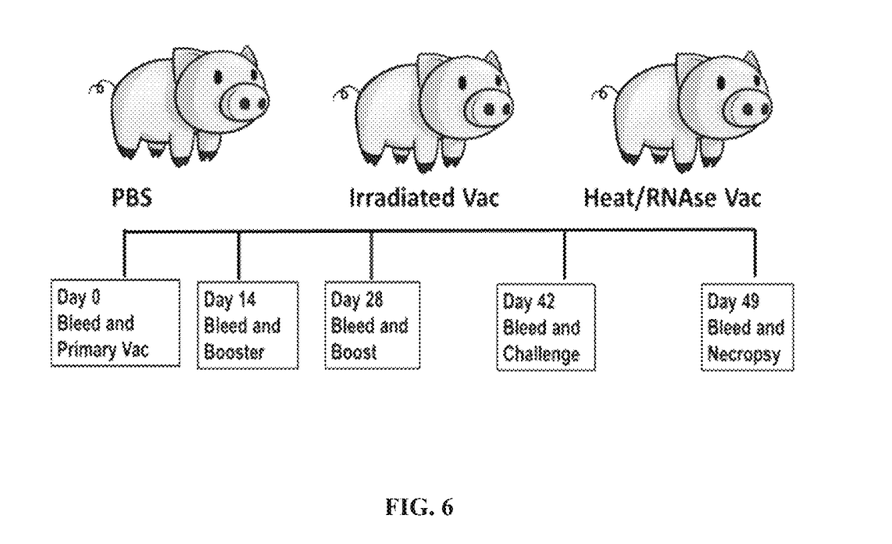

Three groups of 8 pigs each, housed at the South Dakota State University (SDSU) swine experimentation facility, were immunized with A) Sham inoculation B) Irradiated PEDV vaccine C) heat+RNase treated PEDV vaccine. The pigs were boosted twice with the same dose at two week intervals (FIG. 6).

Antibody Responses.

Antibody responses were assessed by a commercial ELISA and virus neutralization assays at the SDSU veterinary diagnostic laboratory. Post-challenge viral loads in fecal matter were assessed by qPCR, using a commercial kit at the NDSU veterinary diagnostic lab. Intestinal tissues were examined for pathology by hematoxylin and eosin sections as well as immunohistochemistry using a PEDV specific antibody.

Figure 7A:
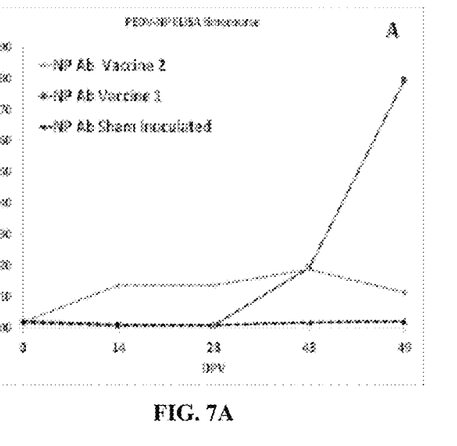
Figure 7B:
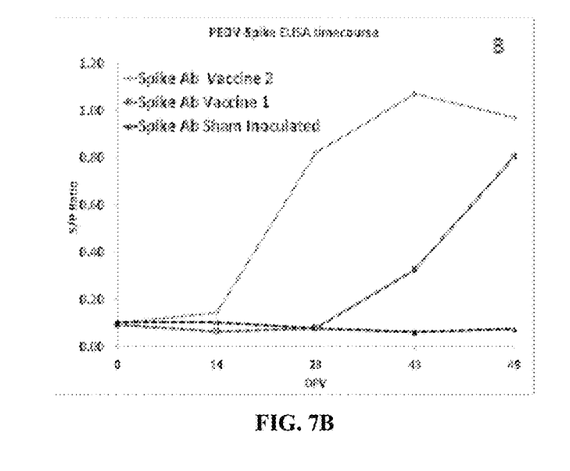
Figure 7C:
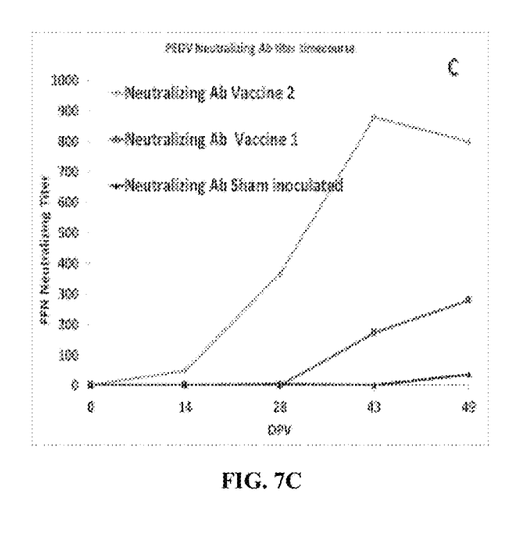

No significant binding antibody responses to the nucleoprotein were detected by ELISA, except at post-challenge for the Vac-I group (FIG. 7A). However, significant responses against the protective spike (S) protein were noted in the Vac-II group and post-challenge for Vac-I (FIG. 7B). Significant virus neutralization titers were detected on DPI 28, following the booster, vaccination for Vac-II, while only low level responses were detected following the second booster and prior to challenge for Vac-I. Following the challenge on DPV 43, significant incremental responses were noted for both vaccine groups (FIG. 7C). The unvaccinated animals showed no responses as expected, except for minimal responses post-challenge (FIG. 7C). The S protein pattern correlated with the virus neutralization data, indicating that Vac-II was stimulating robust antibody responses against the S protein, which in turn were able to neutralize the virus challenge effectively.

Viral Shedding.

Figure 8A:
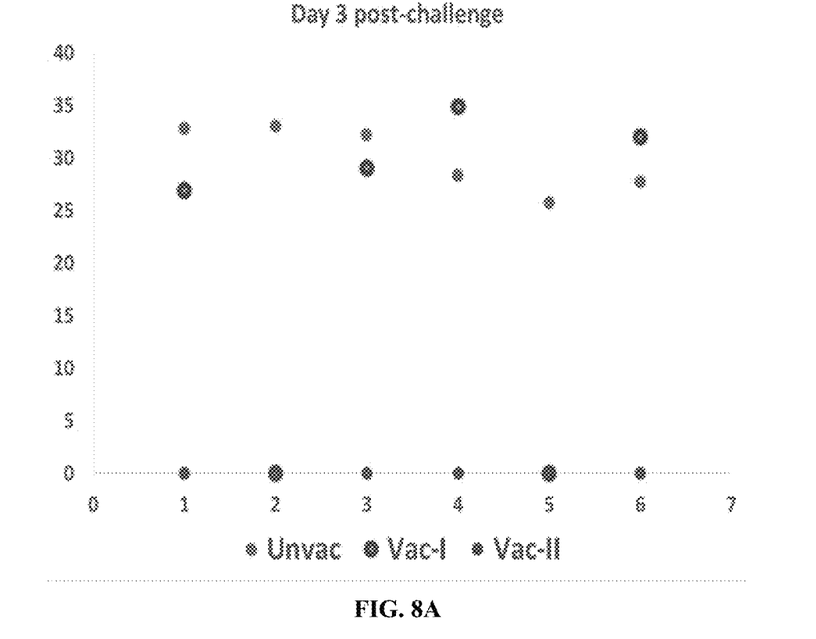
Figure 8B:
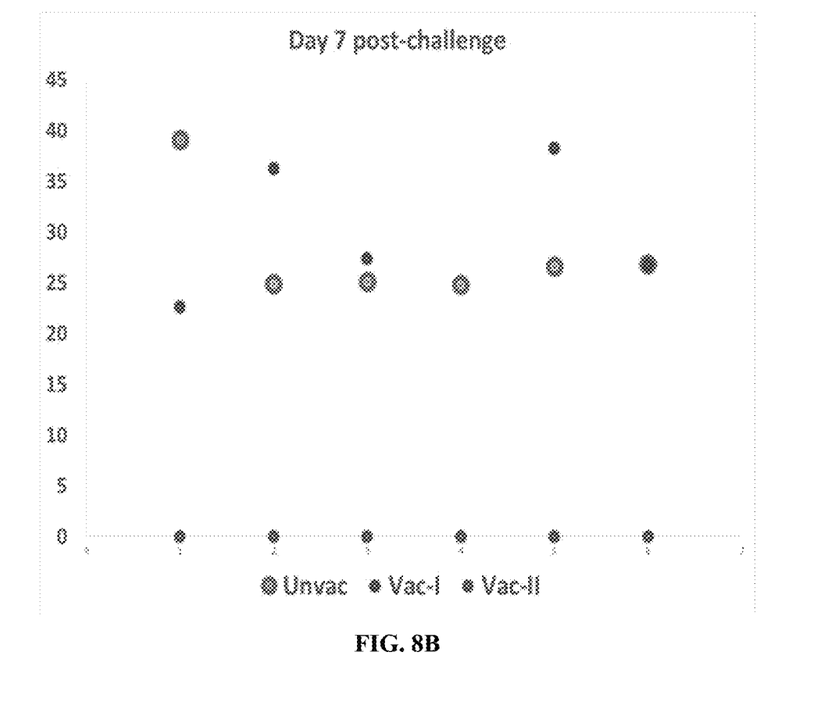

No virus was detected by qPCR at any of the time points prior to challenge in all three groups. At 3 days post challenge all the animals in the heat+RNase treatment showed no viremia, while all animals in the control group were shedding virus in their fecal matter. Four of six animals in the irradiated vaccine group showed shedding (FIG. 8A). At 7 days, post-challenge, the trend continued, with viral shedding increasing in both the unvaccinated controls as well as animals administered the irradiated vaccine, with all 6 animals in the vac-I group turning positive (FIG. 8B). These results indicate that the heat+RNase treated vaccine induced very high levels of protection while the irradiated vaccine did not.

Vaccine-Induced Protection Against Intestinal Lesions.

Figure 9A:
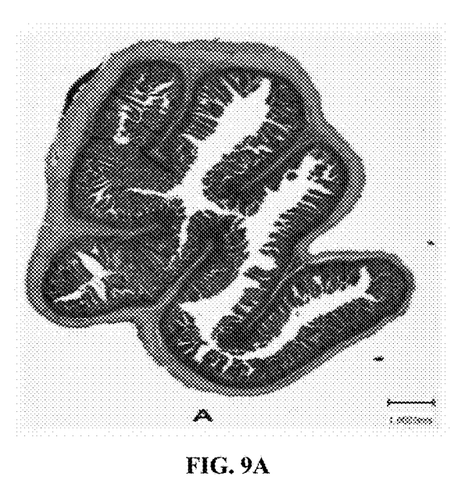
Figure 9B:
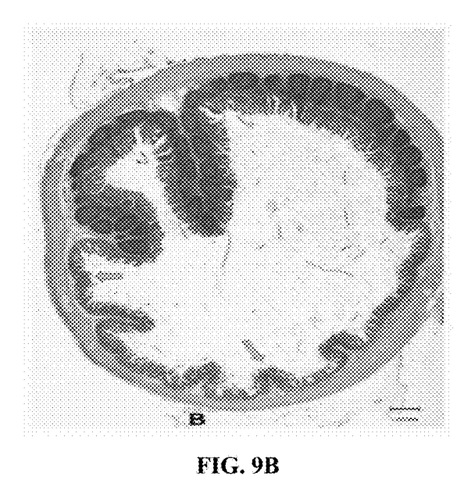
Figure 9C:
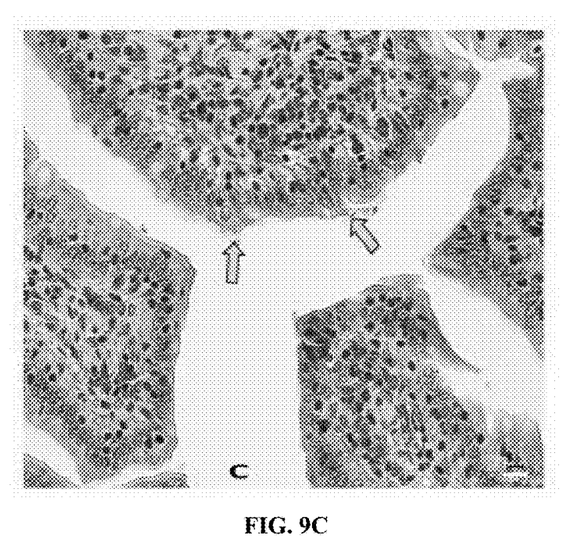
Figure 10A:
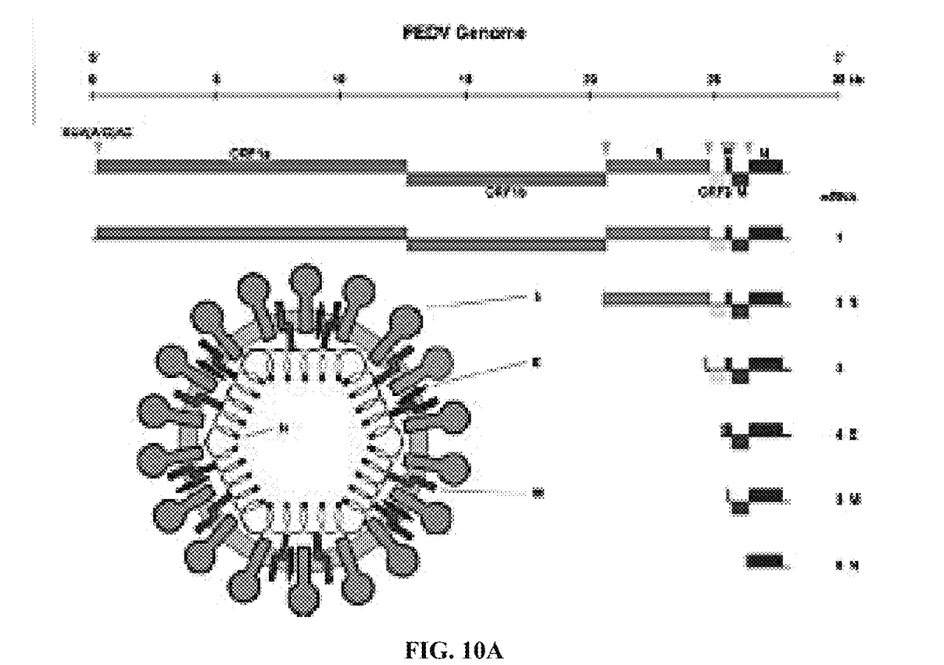
Figure 10B:
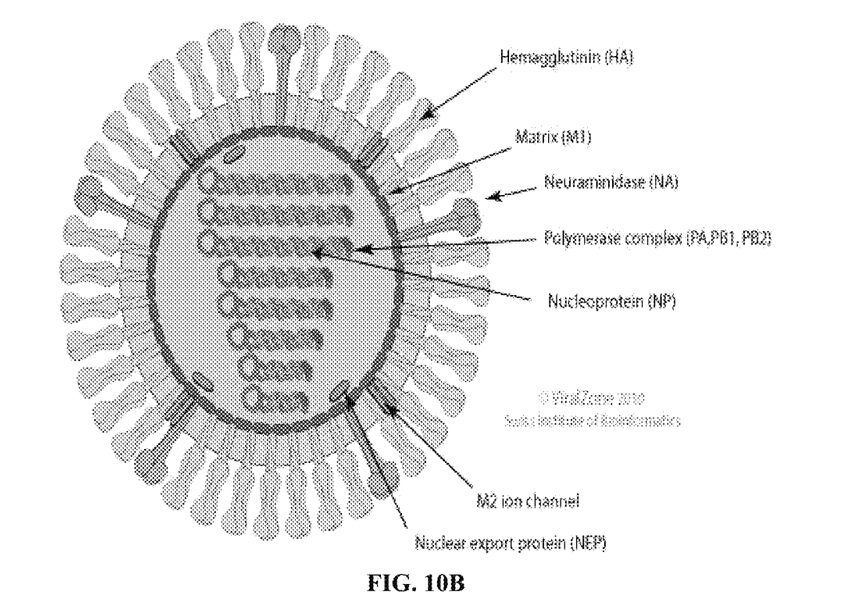

Two slides with three intestinal sections (Ileum, Jejunum and Duodenum) were prepared for each pig for the blinded assessment of microscopic lesions as well as immunohistochemistry (IHC) staining to detect the accumulation of viral antigen in the intestinal cells (FIGS. 9A-C). Scores were assigned as described in Table 1. Very severe lesions were not encountered in any of the groups, including the unvaccinated animals, as the pigs were well over 3 months of age at necropsy. In agreement with the other assessed parameters, the pigs vaccinated with the RNase and heat treated vaccine showed no lesions, and only one out of six pigs had semi-formed stools at necropsy, indicating complete protection by vaccination. Compared to the unvaccinated controls, the pigs administered the irradiated vaccine had higher microscopic scores and comparable IHC scores, but very low fecal scores, indicating that while viral replication occurred on challenge, the high viral titers did not result in clinical signs.

TABLE 1

Lesion scores to assess vaccine-mediated protection against disease.

| Group | Microscopic Lesions* (No. of positive animals/Total animals) | Immuno-histochemistry** (No. of positive animals/Total animals) | Fecal Score*** |
|---|---|---|---|
| Unvaccinated | 4 | 7 | 2.5 |
| | (4/6) | (4/6) | (5/6) |
| Irradiated | 12 | 8 | 0.5 |
| Vaccine | (4/6) | (4/6) | (1/6) |
| RNase + Heat | 0 | 0 | 0.5 |
| Vaccine | (0/6) | (0/6) | (1/6) |

*Mean microscopic lesion scores calculated as the number of positive sections (Ileum, jejunum, duodenum), multiplied by the atrophic enteritis score, where 0 = negative, 1 = mild, 2 = moderate, 3 = severe.
**Mean immunohistochemistry (IHC) score calculated as the number of positive sections (Ileum, jejunum, duodenum), multiplied by the IHC score, where 0 = negative, 1 = positive, ≤10%, 2 = positive, 11-50%, 3 = positive, >50%.
***Fecal score at necropsy-Formed Feces = 0, Semi-formed feces = 3.

Vaccine Safety.

Two pigs from each group were sacrificed prior to challenge to examine whether the vaccines caused any side effects or lead to shedding of the vaccine virus in feces. No virus was detected in the fecal matter at necropsy or after the primary vaccination and boosters, indicating that both vaccines viruses were not amplified or shed in vaccinated animals. Similarly, no microscopic or IHC lesions were detected in these pigs in intestinal, heart, spleen and lung tissues. Therefore, both vaccine development approaches were safe and induced no side effects.

Conclusions.

Of the two approaches used to develop rapid-response first generation vaccines for emerging RNA viruses, the vaccine developed using heat+RNase treatment induced complete protection against challenge with a virulent virus, indicating that this was an excellent and safe process. The pigs vaccinated with the irradiated virus appeared to experience viral replication and developed lesions which were comparable to the unvaccinated controls. However, they did not show clinical signs, indicating that the mechanisms of protection by the two vaccines were likely to be different. The heat+RNase treatment approach was very effective for the inactuation of PEDV and the development of the first response vaccine.

Example 2

Rationale and Methods for Other RNA Viruses.

Although the PEDV virus used in EXAMPLE 1 and IAV are both RNA viruses, the RNA genome organization in PEDV and IAV is very different. The PEDV genome consists of a 12-15 Kb long, positive sense, single strand of RNA. On the other hand, the influenza viral genome consists of 8 short segments of negative-sense RNA, wound around viral non-structural proteins (FIGS. 10A-B).

Mammalian genomes are closely associated with proteins called histones. The histone:DNA association shields the genetic material of the mammalian genome. It was recently found that the influenza NS1 protein, which is closely associated with the viral genome, mimics human histones. Therefore, since very little of the IAV RNA is exposed to digestion by enzymes, it was expected that the inactuation protocol, as used for PEDV, would not be successful with the IAV's. However, similar to the histone:DNA association which can be relaxed through chemical modifications such as acetylation to expose the genetic material, the histone-like motifs found in NS1 can be methylated and acetylated. Accordingly, to inactuate the influenza virus, following heat treatment the virus is first exposed to the histone acetylase enzyme to disrupt the RNA:protein interaction, and then the RNase treatment.

Briefly, the pH1N1 virus was cultured in MDCK cells by standard methods. The virus culture was suspended to $10^4$ $TCID_{50}$/ml. The inactivation treatment was optimized using a series of time points ranging from 1 hour to 12 hours, after exposure to heat at 44° C. for 10 minutes. Assessment of inactivation was carried out as described in EXAMPLE 1, by electron microscopy, PCR and serial passaging of the inactuated virus culture. As an alternative to the heat+enzyme treatment, the gamma-irradiation method may be used to inactivate the virus. Without wishing to be bound by theory, it is expected that the irradiated vaccine will stimulate stronger cell-mediate immunity than antibody-based immunity. Additionally, to improve responses to both arms of the immune response, an adjuvant, such as the Montanide Seppic adjuvant, may be used to improve antibody mediated immunity.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Attia, Y., Schmerold, I., & Honel, A. (2013). The legal foundation of the production and use of herd-specific vaccines in Europe. *Vaccine,* 31(36), 3651-3655. doi: 10.1016/j.vaccine.2013.05.099.
2. Briand, S. (2016). Pandemic and epidemic diseases (PED). http://www.who.int/csr/disease/en/.
3. Duffy, S., Shackelton, L. A., & Holmes, E. C. (2008). Rates of evolutionary change in viruses: patterns and determinants. *Nat Rev Genet,* 9(4), 267-276. doi: 10.1038/nrg2323.
4. Fan, X. (2003). SARS: Economic Impacts and Implications. https://www.adb.org/publications/sars-economic-impacts-and-implications.
5. Immunization, V. a. B. (2008). Vaccine-preventable diseases. http://apps.who.int/immunization_monitoring/diseases/en/.
6. Marazzi, I., Ho, J. S., Kim, J., Manicassamy, B., Dewell, S., Albrecht, R. A., . . . Tarakhovsky, A. (2012). Suppression of the antiviral response by an influenza histone mimic. *Nature,* 483(7390), 428-433. doi: 10.1038/nature10892.
7. Karch, C. P., & Burkhard, P. (2016). Vaccine technologies: From whole organisms to rationally designed protein assemblies. *Biochem Pharmacol,* 120, 1-14. doi: 10.1016/j.bcp 0.2016.05.001.
8. McKenna, M. (2015). Bird Flu Cost the US $3.3 Billion and Worse Could Be Coming. *National Geographic.* http://phenomena.nationalgeographic.com/2015/07/15/bird-flu-2/.
9. Meng, X. J. (2012). Emerging and re-emerging swine viruses. *Transbound Emerg Dis,* 59 Suppl 1, 85-102. doi: 10.1111/j.1865-1682.2011.01291.x.
10. Opriessnig, T., Baker, R. B., & Halbur, P. G. (2007). Use of an experimental model to test the efficacy of planned exposure to live porcine reproductive and respiratory syndrome virus. *Clin Vaccine Immunol,* 14(12), 1572-1577. doi: 10.1128/CVI.00332-07.
11. Sandbulte, M. R., Spickler, A. R., Zaabel, P. K., & Roth, J. A. (2015). Optimal Use of Vaccines for Control of Influenza A Virus in Swine. *Vaccines (Basel),* 3(1), 22-73. doi: 10.3390/vaccines3010022.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for producing an inactuated virus comprising:
    a) forming a denatured viral capsid through heating of the virus to a temperature of between 40° C. and about 44° C. for between 5 and 30 minutes;
    b) exposing viral genetic material within the denatured viral capsid of step (a) to a ribonucleic acid (RNA) degrading enzyme; and
    c) following steps (a) and (b), reestablishing the integrity of the denatured viral capsid through cooling of the virus;
    wherein exposing the viral genetic material to the RNA degrading enzyme in step (b) at least partially destroys the viral genetic material within the denatured viral capsid; and
    wherein steps (a)-(c) are performed without damaging the immunogenic capsid antigens of the virus.
2. The method of claim 1, wherein the virus is porcine epidemic diarrhea virus.
3. The method of claim 1, wherein forming the denatured viral capsid comprises forming pores in the viral capsid.
4. The method of claim 1, wherein forming the denatured viral capsid comprises temporarily relaxing the viral capsid.
5. The method of claim 1, wherein the heating of step (a) is to a temperature of at least 42° C.
6. The method of claim 5, wherein the heating of step (a) is for at least 10 minutes.
7. The method of claim 1, wherein the RNA degrading enzyme is RNase.
8. The method of claim 1, wherein the exposing of step (b) includes exposing the denatured viral capsid to a solution that contains the RNA degrading enzyme.
9. The method of claim 8, wherein the solution includes at least two RNA degrading enzymes.
10. The method of claim 9, wherein the at least two RNA degrading enzymes comprise RNase A and RNase H.
11. The method of claim 1, wherein the exposing of step (b) is for at least 4 hours.
12. The method of claim 1, wherein the cooling of step (c) is to a temperature of 4° C.
13. The method of claim 1, wherein the cooling of step (c) is for at least 3 hours.
14. The method of claim 1, further comprising, after step (a) and before step (b), modifying a protein within the virus.
15. The method of claim 14, wherein the modifying relaxes an RNA:protein association to expose the RNA.
16. The method of claim 14, wherein the modifying includes acetylation.
17. The method of claim 1, wherein the exposing of step (b) destroys viral genetic material without damaging immunogenic capsid antigens of the virus.
18. A method for producing an inactuated virus comprising:
    a) heating the virus to a temperature of about 42° C. for at least 10 minutes to denature the viral capsid;
    b) exposing viral genetic material within the virus of step (a) to a ribonucleic acid (RNA) degrading enzyme; and c) cooling the virus to a temperature of 4° C. or less for at least 3 hours to reestablish the integrity of the denatured viral capsid;
wherein the exposing in step (b) at least partially destroys the viral genetic material.

* * * * *